(12) United States Patent
Chien et al.

(10) Patent No.: US 6,706,495 B2
(45) Date of Patent: Mar. 16, 2004

(54) STAPHYLOCOCCAL GTPASE OBG NUCLEOTIDE SEQUENCE ENCODING STAPHYLOCOCCAL GTP-BINDING PROTEIN

(75) Inventors: Yueh-tyng Chien, Newton, MA (US); Jason A. Thresher, Somerville, MA (US); C. Richard Wobbe, Lexington, MA (US); Judith M. Healy, Lexington, MA (US)

(73) Assignee: Anadys Pharmaceuticals, San Diego, CA (US)

( * ) Notice: Subject to any disclaimer, the term of this patent is extended or adjusted under 35 U.S.C. 154(b) by 68 days.

(21) Appl. No.: 09/792,420

(22) Filed: Feb. 23, 2001

(65) Prior Publication Data

US 2002/0055138 A1 May 9, 2002

Related U.S. Application Data

(60) Provisional application No. 60/184,742, filed on Feb. 24, 2000.

(51) Int. Cl.[7] ................................................. C12P 21/06
(52) U.S. Cl. .................. 435/69.1; 435/69.3; 435/320.1; 435/325; 435/362; 435/365; 435/367; 435/252.3; 435/252.33; 435/69.7; 536/23.7
(58) Field of Search .............................. 435/69.1, 69.3, 435/320.1, 325, 362, 365, 367, 252.3, 252.33, 69.7; 536/23.7

(56) References Cited

U.S. PATENT DOCUMENTS

| | | |
|---|---|---|
| 5,585,277 A | 12/1996 | Bowie et al. |
| 5,679,582 A | 10/1997 | Bowie et al. |
| 5,885,805 A | 3/1999 | Lonetto et al. |

FOREIGN PATENT DOCUMENTS

| | | |
|---|---|---|
| EP | 0 786 519 A2 | 7/1997 |

OTHER PUBLICATIONS

Membrane Associated GTPases in Bacteria, by March, Molecular Microbiol, vol. 6, pp. 1253–1257, 1992.

"The *Bacillus subtilis* spoOB Stage O Sporulation Operon Encodes an Essential GTP–Binding Protein" by Trach et al., J. Bacteriol, vol. 171, pp. 1362–1371, 1989.

"Biochemical Characterization of the Essential GTP–Binding Protein Obg of *Bacillus subtilis*" by Welsh et al., J. Bacteriol, vol. 176, pp. 7161–7168, 1994.

"Effects on *Bacillus subtilis* of a Conditional Lethal Mutation in the Essential GTP–Binding Protein Obg", Kok et al., J. Bacteriol, vol. 176, pp. 7155–7160.

"Molecular Cloning and Characterization of the obg Gene of *Streptomyces griseus* in Relation to the Onset of Morphological Differentiation" Okamoto et al., J. Bacteriol, vol. 179, pp. 170–179, 1997.

"Identification of an Essential *Caulobacter crescentus* Gene Encoding a Member of the Obg Family of GTP–Binding Proteins", Maddock et al., J. Bacteriol, vol. 179, pp. 6426–6431, 1997.

"A Genome–Based Approach for the Identification of Essential Bacterial Genes", Arigoni et al., Nature Biotechnology, vol. 16, pp. 851–856 1998.

"Possible Role for the Essential GTP–Binding Protein Obg in Regulating the Initiation of Sporulation in *Bacillus subtilis*" Vidwans et al., J. Bacteriol, vol. 177, pp. 3308–3311, 1985.

"Phylogenetic Inference" by Swofford et al., Molecular Systematics, Sinauer Associates, Inc., pp. 407–514, 1996.

"Nucleotide Sequence of nifD from Frankia alni Strain ArI3: Phylogenetic Inferences", Normand et al., Mol. Biol. Evol., vol. 9, pp. 495–506, 1992.

*Primary Examiner*—Jennifer E. Graser
(74) *Attorney, Agent, or Firm*—David R. Preston & Associates; David Preston

(57) ABSTRACT

The present invention provides an isolated Staphylococcal GTPase obg gene and a Staphylococcal GTP-binding protein encoded thereby. A recombinant expression vector and an engineered host cell are also provided that include a polynucleotide encoding a Staphylococcal GTP-binding protein. The present invention further relates to a method of producing Staphylococcal GTP-binding protein and a method for high throughput screening to identify potential antimicrobial compounds useful against Staphylococcal bacterial strains.

34 Claims, 5 Drawing Sheets

```
obg--->
1/1                                          31/11
ATG TTT GTG GAT CAA GTC AAA ATA TCT CTT AAA GCC GGT GAT GGT GGT AAT GGT ATT ACC
 M   F   V   D   Q   V   K   I   S   L   K   A   G   D   G   G   N   G   I   T
61/21                                        91/31
GCA TAC AGA AGA GAA AAA TAT GTA CCA TTT GGT GGA CCA GCT GGC GGT GAC GGT GGT AAA
 A   Y   R   R   E   K   Y   V   P   F   G   G   P   A   G   G   D   G   G   K
121/41                                       151/51
GGT GCT TCA GTC GTA TTT GAA GTG GAT GAA GGT TTA AGA ACG TTA TTA GAT TTT AGA TAT
 G   A   S   V   V   F   E   V   D   E   G   L   R   T   L   L   D   F   R   Y
181/61                                       211/71
CAA CGT CAT TTT AAA GCA AGC AAA GGT GAA AAT GGC CAA AGT AGT AAT ATG CAT GGT AAA
 Q   R   H   F   K   A   S   K   G   E   N   G   Q   S   S   N   M   H   G   K
241/81                                       271/91
AAT GCG GAA GAT TTA GTA TTA AAA GTT CCA CCT GGT ACA ATT ATT AAA AAT GTT GAA ACA
 N   A   E   D   L   V   L   K   V   P   P   G   T   I   I   K   N   V   E   T
301/101                                      331/111
GAC GAA GTG TTA GCA GAT CTT GTT GAA GAT GGT CAA AGA GCT GTA GTA GCG AAG GGC GGT
 D   E   V   L   A   D   L   V   E   D   G   Q   R   A   V   V   A   K   G   G
361/121                                      391/131
CGA GGT GGC CGA GGT AAT TCA CGT TTT GCA ACA CCT AGA AAC CCT GCA CCT GAC TTC AGT
 R   G   G   R   G   N   S   R   F   A   T   P   R   N   P   A   P   D   F   S
421/141                                      451/151
GAA AAA GGT GAA CCA GGT GAG GAA TTA GAT GTA TCT TTA GAA TTG AAA TTA TTA GCT GAT
 E   K   G   E   P   G   E   E   L   D   V   S   L   E   L   K   L   L   A   D
481/161                                      511/171
GTA GGA TTA GTA GGT TTC CCT AGT GTG GGT AAA TCG ACT TTA TTA TCT ATC GTT TCA AAA
 V   G   L   V   G   F   P   S   V   G   K   S   T   L   L   S   I   V   S   K
541/181                                      571/191
GCT AAG CCT AAA ATT GGG GCA TAT CAT TTT ACA ACG ATT AAA CCA AAT CTA GGT GTT GTT
 A   K   P   K   I   G   A   Y   H   F   T   T   I   K   P   N   L   G   V   V
601/201                                      631/211
TCA ACG CCT GAT CAA CGT AGT TTT GTT ATG GCA GAT TTA CCA GGT TTA ATT GAA GGT GCA
 S   T   P   D   Q   R   S   F   V   M   A   D   L   P   G   L   I   E   G   A
661/221                                      691/231
TCT GAT GGC GTT GGA TTA GGA CAT CAA TTT TTA AGA CAT GTA GAG AGA ACA AAA GTT ATT
 S   D   G   V   G   L   G   H   Q   F   L   R   H   V   E   R   T   K   V   I
721/241                                      751/251
GTT CAC ATG ATT GAT ATG AGC GGT TCT GAA GGT AGA GAA CCT ATT GAA GAT TAT AAA GTC
 V   H   M   I   D   M   S   G   S   E   G   R   E   P   I   E   D   Y   K   V
781/261                                      811/271
ATT AAT CAA GAA TTA GCT GCG TAC GAG CAA CGT TTA GAA GAT AGA CCT CAA ATC GTA GTA
 I   N   Q   E   L   A   A   Y   E   Q   R   L   E   D   R   P   Q   I   V   V
841/281                                      871/291
GCT AAC AAG ATG GAT TTA CCT GAA TCA CAA GAT AAT TTA AAC TTG TTT AAA GAA GAA ATT
 A   N   K   M   D   L   P   E   S   Q   D   N   L   N   L   F   K   E   E   I
901/301                                      931/311
GGC GAA GAT GTG CCA GTT ATT CCA GTT TCA ACA ATA ACG CGT GAT AAT ATT GAT CAA TTA
 G   E   D   V   P   V   I   P   V   S   T   I   T   R   D   N   I   D   Q   L
961/321                                      991/331
TTA TAT GCA ATA GCA GAT AAA TTA GAA GAA TAT AAA GAT GTT GAC TTC ACA GTT GAA GAA
 L   Y   A   I   A   D   K   L   E   E   Y   K   D   V   D   F   T   V   E   E
1021/341                                     1051/351
GAG GAG TCA GTT GGC ATT AAC CGA GTA TTA TAT AAA CAT ACA CCG TCA CAA GAT AAA TTT
 E   E   S   V   G   I   N   R   V   L   Y   K   H   T   P   S   Q   D   K   F
1081/361                                     1111/371
ACA ATT TCA AGA GAT GAT GAT GGT GCT TAT GTG GTA AGT GGT AAT GCT ATT GAA AGA ATG
 T   I   S   R   D   D   D   G   A   Y   V   V   S   G   N   A   I   E   R   M
1141/381                                     1171/391
TTT AAA ATG ACT GAC TTT AAC AGT GAT CCA GCA GTA CGT CGA TTT GCT CGT CAA ATG CGT
 F   K   M   T   D   F   N   S   D   P   A   V   R   R   F   A   R   Q   M   R
1201/401                                     1231/411
TCG ATG GGT ATT GAT GAT GCG CTT AGA GAA CGT GGT TGT AAA AAT GGT GAT ATC GTT AGA
 S   M   G   I   D   D   A   L   R   E   R   G   C   K   N   G   D   I   V   R
1261/421                                     1291/431
ATT CTT GGC GGA GAA TTT GAA TTC GTT GAA TAA   (SEQ ID NO:1)
 I   L   G   G   E   F   E   F   V   E   *    (SEQ ID NO:2)
```

Fig. 1

Sequence alignment of obg from a variety of bacteria.

```
E._faecali   NRRTNYMSMFLDQVTIDVKAGKGGDGMVAFRREKYVPDGGPAGGDGGRGGDVVLVVEEGL
E._faecium   --EDLIMSMFLDQVTIDVKAGKGGDGMVAFRREKYVPDGGPAGGDGGRGGDVILIVDEGL
Streptococ   ---EEIMSMFLDTAKIKVKAGNGGDGMVAFRREKYVPNGGPWGGDGGRGGNVVFVVDEGL
Bacillus_s   --------MFVDQVKVYVKGGDGGNGMVAFRREKYVPKGGPAGGDGGKGGDVVFEVDEGL
Staph_aure   --------MFVDQVKISLKAGDGGNGITAYRREKYVPFGGPAGGDGGKGASVVFEVDEGL
Clos_aceto   --------MFVDKARIFVKSGDGGDGAVSFRREKYIPLGGPDGGDGGEGGDVILVVDPNM
                     **.*   . .* * ** *  ..***** * *** ***** *  *. .*. ..

E._faecali   RTLMDFRFNRHFKATPGENGMSKGMHGRGSEDLLVKVPPGTTVRDAETGALIGDLIENGQ
E._faecium   RTLMDFRFNRHFKAQPGENGMSKGMHGRGSEHTYVKVPQGTTVRDAETGALLGDLIENGQ
Streptococ   RTLMDFRYNRHFKADSGEKGMTKGMHGRGAEDLRVRVSQGTTVRDAETGKVLTDLIKHGQ
Bacillus_s   RTLMDFRYKKHFKAIRGEHGMSKNQHGRNADDMVIKVPPGTVVTDDDTKQVIADLTEHGQ
Staph_aure   RTLLDFRYQRHFKASKGENGQSSNMHGKNAEDLVLKVPPGTIIKNVETDEVLADLVEDGQ
Clos_aceto   TTLLDFKYKRKYVSERGQNGQGAKCYGRDGKDLYIKVPMGTIIRDVETDKIMADLAHKDD
             **.**.. ... .  *. *            *.      ..*  **  .  *  .. **

E._faecali   TLVVAKGGRGGRGNIRFASPRNPAPEIAENGEPGQERKIELELKVLADVGLVGFPSVGKS
E._faecium   TLVVAKGGRGGRGNIRFASPRNPAPEIAENGEPGQERKIELELKVLADVGLVGFPSVGKS
Streptococ   EFIVAHGGRGGRGNIRFATPKNPAPEISENGEPGQERELQLELKILADVGLVGFPSVGKS
Bacillus_s   RAVIARGGRGGRGNSRFATPANPAPQLSENGEPGKERYIVLELKVLADVGLVGFPSVGKS
Staph_aure   RAVVAKGGRGGRGNSRFATPRNPAPDFSEKGEPGEELDVSLELKLLADVGLVGFPSVGKS
Clos_aceto   KFVIVKGGRGGKGNVKFCTPTRQAPNFAQPGMPGEERWISLELKLLADVGLIGFPNVGKS
             .. .*****.**  .*..*   **   ..  * ** *   . ****.***** .*** ****

E._faecali   TLLSVISSARPKIGAYHFTTLVPNLGMVTTSDGRSFAAADLPGLIEGASQGVGLGTQFLR
E._faecium   TLLSVISSARPKIGAYHFTTLVPNLGMVTTSDGRSFAAADLPGLIEGASQGVGLGTQFLR
Streptococ   TLLSVITSAKPKIGAYHFTTIVPNLGMVRTQSGESFAVADLPGLIEGASQGVGLGTQFLR
Bacillus_s   TLLSVVSSAKPKIADYHFTTLVPNLGMVETDDGRSFVMADLPGLIEGAHQGVGLGHQFLR
Staph_aure   TLLSIVSKAKPKIGAYHFTTIKPNLGVVSTPDQRSFVMADLPGLIEGASDGVGLGHQFLR
Clos_aceto   TLLSVASKARPKIAKYHFTTITPNLGVVDVSGISSFVMADIPGIIEGASEGVGLGFEFLR
             ****.  . *.***  *****. ****.*       ** **.**.**** ***** .***

E._faecali   HIERTRVILHVIDMSGMEGRDPYEDYLAINKELASHNLRLMERPQIIVANKMDMPEAEEN
E._faecium   HIERTRVILHVIDMSGMEGRDPYEDYLAINKELSTYNLRLLERPQIIVANKMDMPDAPEN
Streptococ   HIERTRVILHIIDMSASEGRDPYEDYLAINKELESYNLRLMERPQIIVANKMDMPESQEN
Bacillus_s   HIERTRVIVHVIDMSGLEGRDPYDDYLTINQELSEYNLRLTERPQIIVANKMDMPEAAEN
Staph_aure   HVERTKVIVHMIDMSGSEGREPIEDYKVINQELAAYEQRLEDRPQIVVANKMDLPESQDN
Clos_aceto   HIERTRLLVHVVDISGSEGRDPLEDFLKINEELKKYNIKLWDRPQIVAANKADMVYDDDQ
             *.***....*...*.*   ***.*  .*.  ** **      .* .****. *** *.

E._faecali   LAKFKEQLAKERTDEYADELPIFPISGVTRKGIEPLLNATADLLEVTP--EFPLYEDEVV
E._faecium   LVKFKEQLNKEKEDEFADDIPVFPISGVTRQGLDALLNATADLLEVTP--EFPLYEEEL-
Streptococ   LEEFKKKLAEN-YDEFEELPAIFPISGLTKQGLATLLLDATAELLDKTP--EFLLYDESD-
Bacillus_s   LEAFKEKLTDD--------YPVFPISAVTREGLRELLFEVANQLENTP--EFPLYDEEEL
Staph_aure   LNLFKEEIGED--------VPVIPVSTITRDNIDQLLYAIADKLEEYKDVDFTVEEEESV
Clos_aceto   FNKFREELNKLG------YKNVFKISAATRMGVEDLLKECARVLSTIPVTDMEIPEEER-
              *. .              . .* *.  ..  ** *.  ..  **  * *   . ....
```

Fig. 2

```
E._faecali   EEETVRYGFQPEGPEFTIDREPDASWVLSGEKLEKLFEMTNFDHDETVMRFARQLRGMGV
E._faecium   EEETVHYGFNPEGPEFQIDRDSDATWILSGEKIEKLFQMTNFDHDETVMRFARQLRGMGV
Streptococ   MEEEAYYGFDEEEKAFEISRDDDATWVLSGEKLMKLFNMTNFDRDESVMKFARQLRGMGV
Bacillus_s   TQNRVMYTMENEEVPFNITRDPDGVFVLSGDSLERLFKMTDFSRDESVKRFARQMRGMGV
Staph_aure   GINRVLYKHTPSQDKFTISRDDDGAYVVSGNAIERMFKMTDFNSDPAVRRFARQMRSMGI
Clos_aceto   ----FVPED--KHFTYTIRKEGD-TYIVEGTFVDRLLASVNVNEPDSFRYFHKVLRNKGV
                 .  *  .. *    .. *   . . .         . *  . *   *.

E._faecali   DEALRARGAKDGDIVRIGNFEFEFVE-    (SEQ ID NO:5)
E._faecium   DEALRARGAKDGDLVRIGEFEFEFVE-    (SEQ ID NO:6)
Streptococ   DEALRARGAKDGDLVRIGKFEFEFVD-    (SEQ ID NO:7)
Bacillus_s   DEALRERGAKDGDIIRLLEFEFEFID-    (SEQ ID NO:8)
Staph_aure   DDALRERGCKNGDIVRILGGEFEFVEZ    (SEQ ID NO:2)
Clos_aceto   MAELEEMGIKDGDMVRLNDFEFEFLK-    (SEQ ID NO:9)
                *    *  * **..*.    ****.
```

Fig. 2 (continued)

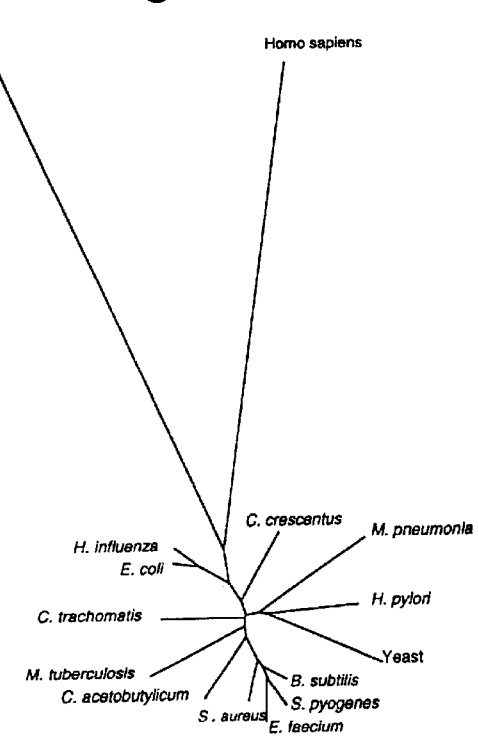

Fig. 3

Lane: 1 2 3 4 5
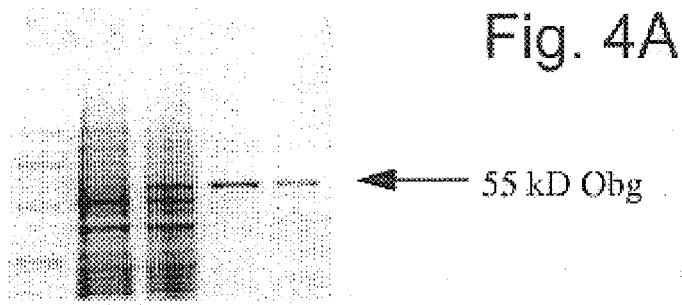
Fig. 4A
← 55 kD Obg
Lane: 1. SeeBlue molecular weight marker
2. pET14b alone [in BL21(DE3).pLys.S]
3. pET14b + obg [in BL21(DE3).pLys.S]
4. Obg batch #1 fraction from Ni column
5. Obg batch #2 fraction from Ni column
Fig. 4B
Western Blot
Anti-His-tag antibody                Polyclonal antibody against *Caulobacter* Obg
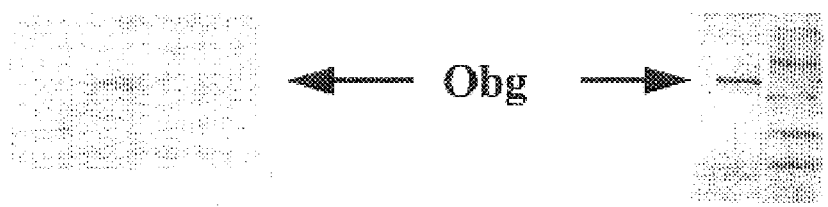
← Obg →

SEQUENCE LISTING

<160> NUMBER OF SEQ ID NOS: 11

<210> SEQ ID NO 1
<211> LENGTH: 1293
<212> TYPE: DNA
<213> ORGANISM: Staphylococcus aureus

<400> SEQUENCE: 1

| | | | | | |
|---|---|---|---|---|---|
| atgtttgtgg | atcaagtcaa | aatatctctt | aaagccggtg | atggtggtaa | tggtattacc | 60 |
| gcatacagaa | gagaaaaata | tgtaccattt | ggtggaccag | ctggcggtga | cggtggtaaa | 120 |
| ggtgcttcag | tcgtatttga | agtggatgaa | ggtttaagaa | cgttattaga | ttttagatat | 180 |
| caacgtcatt | ttaaagcaag | caaaggtgaa | aatggccaaa | gtagtaatat | gcatggtaaa | 240 |
| aatgcggaag | atttagtatt | aaaagttcca | cctggtacaa | ttattaaaaa | tgttgaaaca | 300 |
| gacgaagtgt | tagcagatct | tgttgaagat | ggtcaaagag | ctgtagtagc | gaagggcggt | 360 |
| cgaggtggcc | gaggtaattc | acgttttgca | cacctagaa | accctgcacc | tgacttcagt | 420 |
| gaaaaaggtg | aaccaggtga | ggaattagat | gtatctttag | aattgaaatt | attagctgat | 480 |
| gtaggattag | taggtttccc | tagtgtgggt | aaatcgactt | tattatctat | cgtttcaaaa | 540 |
| gctaagccta | aaattggggc | atatcatttt | acaacgatta | aaccaaatct | aggtgttgtt | 600 |
| tcaacgcctg | atcaacgtag | ttttgttatg | gcagatttac | caggtttaat | tgaaggtgca | 660 |
| tctgatggcg | ttgattaagg | acatcaattt | ttaagacatg | tagagagaac | aaaagttatt | 720 |
| gttcacatga | ttgatatgag | cggttctgaa | ggtagagaac | ctattgaaga | ttataaagtc | 780 |
| attaatcaag | aattagctgc | gtacgagcaa | cgtttagaag | atagacctca | aatcgtagta | 840 |
| gctaacaaga | tggatttacc | tgaatcacaa | gataatttaa | acttgtttaa | agaagaaatt | 900 |
| ggcgaagatg | tgccagttat | tccagtttca | acaataacgc | gtgataatat | tgatcaatta | 960 |
| ttatatgcaa | tagcagataa | attagaagaa | tataaagatg | ttgacttcac | agttgaagaa | 1020 |
| gaggagtcag | ttggcattaa | ccgagtatta | tataaacata | caccgtcaca | agataaatttt | 1080 |
| acaatttcaa | gagatgatga | tggtgcttat | gtggtaagtg | gtaatgctat | tgaaagaatg | 1140 |
| tttaaaatga | ctgactttaa | cagtgatcca | gcagtacgtc | gatttgctcg | tcaaatgcgt | 1200 |
| tcgatgggta | ttgatgatgc | gcttagagaa | cgtggttgta | aaaatggtga | tatcgttaga | 1260 |
| attcttggcg | gagaatttga | attcgttgaa | taa | | | 1293 |

<210> SEQ ID NO 2
<211> LENGTH: 430
<212> TYPE: PRT
<213> ORGANISM: Staphylococcus aureus

<400> SEQUENCE: 2

Met Phe Val Asp Gln Val Lys Ile Ser Leu Lys Ala Gly Asp Gly Gly
1               5                   10                  15

Asn Gly Ile Thr Ala Tyr Arg Arg Glu Lys Tyr Val Pro Phe Gly Gly
            20                  25                  30

Pro Ala Gly Gly Asp Gly Gly Lys Gly Ala Ser Val Val Phe Glu Val
        35                  40                  45

Asp Glu Gly Leu Arg Thr Leu Leu Asp Phe Arg Tyr Gln Arg His Phe
    50                  55                  60

Lys Ala Ser Lys Gly Glu Asn Gly Gln Ser Ser Asn Met His Gly Lys
65                  70                  75                  80

```
Asn Ala Glu Asp Leu Val Leu Lys Val Pro Pro Gly Thr Ile Ile Lys
                85                  90                  95

Asn Val Glu Thr Asp Glu Val Leu Ala Asp Leu Val Glu Asp Gly Gln
            100                 105                 110

Arg Ala Val Val Ala Lys Gly Gly Arg Gly Gly Arg Gly Asn Ser Arg
        115                 120                 125

Phe Ala Thr Pro Arg Asn Pro Ala Pro Asp Phe Ser Glu Lys Gly Glu
    130                 135                 140

Pro Gly Glu Glu Leu Asp Val Ser Leu Glu Leu Lys Leu Leu Ala Asp
145                 150                 155                 160

Val Gly Leu Val Gly Phe Pro Ser Val Gly Lys Ser Thr Leu Leu Ser
                165                 170                 175

Ile Val Ser Lys Ala Lys Pro Lys Ile Gly Ala Tyr His Phe Thr Thr
            180                 185                 190

Ile Lys Pro Asn Leu Gly Val Val Ser Thr Pro Asp Gln Arg Ser Phe
        195                 200                 205

Val Met Ala Asp Leu Pro Gly Leu Ile Glu Gly Ala Ser Asp Gly Val
    210                 215                 220

Gly Leu Gly His Gln Phe Leu Arg His Val Glu Arg Thr Lys Val Ile
225                 230                 235                 240

Val His Met Ile Asp Met Ser Gly Ser Glu Gly Arg Glu Pro Ile Glu
                245                 250                 255

Asp Tyr Lys Val Ile Asn Gln Glu Leu Ala Ala Tyr Glu Gln Arg Leu
            260                 265                 270

Glu Asp Arg Pro Gln Ile Val Val Ala Asn Lys Met Asp Leu Pro Glu
        275                 280                 285

Ser Gln Asp Asn Leu Asn Leu Phe Lys Glu Glu Ile Gly Glu Asp Val
    290                 295                 300

Pro Val Ile Pro Val Ser Thr Ile Thr Arg Asp Asn Ile Asp Gln Leu
305                 310                 315                 320

Leu Tyr Ala Ile Ala Asp Lys Leu Glu Glu Tyr Lys Asp Val Asp Phe
                325                 330                 335

Thr Val Glu Glu Glu Ser Val Gly Ile Asn Arg Val Leu Tyr Lys
            340                 345                 350

His Thr Pro Ser Gln Asp Lys Phe Thr Ile Ser Arg Asp Asp Gly
        355                 360                 365

Ala Tyr Val Val Ser Gly Asn Ala Ile Glu Arg Met Phe Lys Met Thr
    370                 375                 380

Asp Phe Asn Ser Asp Pro Ala Val Arg Arg Phe Ala Arg Gln Met Arg
385                 390                 395                 400

Ser Met Gly Ile Asp Asp Ala Leu Arg Glu Arg Gly Cys Lys Asn Gly
                405                 410                 415

Asp Ile Val Arg Ile Leu Gly Gly Glu Phe Glu Phe Val Glu
            420                 425                 430

<210> SEQ ID NO 3
<211> LENGTH: 26
<212> TYPE: DNA
<213> ORGANISM: Bacillus subtilis
<220> FEATURE:
<221> NAME/KEY: n
<222> LOCATION: (15)..(24)
<223> OTHER INFORMATION: a or g or c or t

<400> SEQUENCE: 3
cgccatatgt tygtngayca rgtnaa                                          26
```

<210> SEQ ID NO 4
<211> LENGTH: 30
<212> TYPE: DNA
<213> ORGANISM: Bacillus subtilis
<220> FEATURE:
<221> NAME/KEY: n
<222> LOCATION: (16)..(16)
<223> OTHER INFORMATION: a or g or c or t

<400> SEQUENCE: 4
ccgctcgagt tattcnacra aytcraaytc                                          30

<210> SEQ ID NO 5
<211> LENGTH: 444
<212> TYPE: PRT
<213> ORGANISM: Enterococcus faecalis

<400> SEQUENCE: 5

```
Asn Arg Arg Thr Asn Tyr Met Ser Met Phe Leu Asp Gln Val Thr Ile
1               5                   10                  15

Asp Val Lys Ala Gly Lys Gly Gly Asp Gly Met Val Ala Phe Arg Arg
            20                  25                  30

Glu Lys Tyr Val Pro Asp Gly Gly Pro Ala Gly Gly Asp Gly Gly Arg
        35                  40                  45

Gly Gly Asp Val Val Leu Val Val Glu Glu Gly Leu Arg Thr Leu Met
    50                  55                  60

Asp Phe Arg Phe Asn Arg His Phe Lys Ala Thr Pro Gly Glu Asn Gly
65                  70                  75                  80

Met Ser Lys Gly Met His Gly Arg Gly Ser Glu Asp Leu Leu Val Lys
                85                  90                  95

Val Pro Pro Gly Thr Thr Val Arg Asp Ala Glu Thr Gly Ala Leu Ile
            100                 105                 110

Gly Asp Leu Ile Glu Asn Gly Gln Thr Leu Val Val Ala Lys Gly Gly
        115                 120                 125

Arg Gly Gly Arg Gly Asn Ile Arg Phe Ala Ser Pro Arg Asn Pro Ala
    130                 135                 140

Pro Glu Ile Ala Glu Asn Gly Glu Pro Gly Gln Glu Arg Lys Ile Glu
145                 150                 155                 160

Leu Glu Leu Lys Val Leu Ala Asp Val Gly Leu Val Gly Phe Pro Ser
                165                 170                 175

Val Gly Lys Ser Thr Leu Leu Ser Val Ile Ser Ser Ala Arg Pro Lys
            180                 185                 190

Ile Gly Ala Tyr His Phe Thr Thr Leu Val Pro Asn Leu Gly Met Val
        195                 200                 205

Thr Thr Ser Asp Gly Arg Ser Phe Ala Ala Asp Leu Pro Gly Leu
    210                 215                 220

Ile Glu Gly Ala Ser Gln Gly Val Gly Leu Gly Thr Gln Phe Leu Arg
225                 230                 235                 240

His Ile Glu Arg Thr Arg Val Ile Leu His Val Ile Asp Met Ser Gly
                245                 250                 255

Met Glu Gly Arg Asp Pro Tyr Glu Asp Tyr Leu Ala Ile Asn Lys Glu
            260                 265                 270

Leu Ala Ser His Asn Leu Arg Leu Met Glu Arg Pro Gln Ile Ile Val
        275                 280                 285

Ala Asn Lys Met Asp Met Pro Glu Ala Glu Glu Asn Leu Ala Lys Phe
    290                 295                 300
```

```
Lys Glu Gln Leu Ala Lys Glu Arg Thr Asp Glu Tyr Ala Asp Glu Leu
305                 310                 315                 320

Pro Ile Phe Pro Ile Ser Gly Val Thr Arg Lys Gly Ile Glu Pro Leu
                325                 330                 335

Leu Asn Ala Thr Ala Asp Leu Leu Glu Val Thr Pro Glu Phe Pro Leu
                340                 345                 350

Tyr Glu Asp Glu Val Val Glu Glu Thr Val Arg Tyr Gly Phe Gln
                355                 360                 365

Pro Glu Gly Pro Glu Phe Thr Ile Asp Arg Glu Pro Asp Ala Ser Trp
        370                 375                 380

Val Leu Ser Gly Glu Lys Leu Glu Lys Leu Phe Glu Met Thr Asn Phe
385                 390                 395                 400

Asp His Asp Glu Thr Val Met Arg Phe Ala Arg Gln Leu Arg Gly Met
                405                 410                 415

Gly Val Asp Glu Ala Leu Arg Ala Arg Gly Ala Lys Asp Gly Asp Ile
                420                 425                 430

Val Arg Ile Gly Asn Phe Glu Phe Glu Phe Val Glu
            435                 440

<210> SEQ ID NO 6
<211> LENGTH: 441
<212> TYPE: PRT
<213> ORGANISM: Enterococcus faecium

<400> SEQUENCE: 6

Glu Asp Leu Ile Met Ser Met Phe Leu Asp Gln Val Thr Ile Asp Val
1               5                   10                  15

Lys Ala Gly Lys Gly Gly Asp Gly Met Val Ala Phe Arg Arg Glu Lys
                20                  25                  30

Tyr Val Pro Asp Gly Gly Pro Ala Gly Gly Asp Gly Gly Arg Gly Gly
            35                  40                  45

Asp Val Ile Leu Ile Val Asp Glu Gly Leu Arg Thr Leu Met Asp Phe
        50                  55                  60

Arg Phe Asn Arg His Phe Lys Ala Gln Pro Gly Glu Asn Gly Met Ser
65                  70                  75                  80

Lys Gly Met His Gly Arg Gly Ser Glu His Thr Tyr Val Lys Val Pro
                85                  90                  95

Gln Gly Thr Thr Val Arg Asp Ala Glu Thr Gly Ala Leu Leu Gly Asp
                100                 105                 110

Leu Ile Glu Asn Gly Gln Thr Leu Val Val Ala Lys Gly Gly Arg Gly
            115                 120                 125

Gly Arg Gly Asn Ile Arg Phe Ala Ser Pro Arg Asn Pro Ala Pro Glu
        130                 135                 140

Ile Ala Glu Asn Gly Glu Pro Gly Gln Glu Arg Lys Ile Glu Leu Glu
145                 150                 155                 160

Leu Lys Val Leu Ala Asp Val Gly Leu Val Gly Phe Pro Ser Val Gly
                165                 170                 175

Lys Ser Thr Leu Leu Ser Val Ile Ser Ser Ala Arg Pro Lys Ile Gly
            180                 185                 190

Ala Tyr His Phe Thr Thr Leu Val Pro Asn Leu Gly Met Val Thr Thr
        195                 200                 205

Ser Asp Gly Arg Ser Phe Ala Ala Ala Asp Leu Pro Gly Leu Ile Glu
    210                 215                 220

Gly Ala Ser Gln Gly Val Gly Leu Gly Thr Gln Phe Leu Arg His Ile
```

-continued

```
                225                 230                 235                 240

Glu Arg Thr Arg Val Ile Leu His Val Ile Asp Met Ser Gly Met Glu
                    245                 250                 255

Gly Arg Asp Pro Tyr Glu Asp Tyr Leu Ala Ile Asn Lys Glu Leu Ser
                260                 265                 270

Thr Tyr Asn Leu Arg Leu Leu Glu Arg Pro Gln Ile Ile Val Ala Asn
                275                 280                 285

Lys Met Asp Met Pro Asp Ala Pro Glu Asn Leu Val Lys Phe Lys Glu
            290                 295                 300

Gln Leu Asn Lys Glu Lys Glu Asp Glu Phe Ala Asp Asp Ile Pro Val
305                 310                 315                 320

Phe Pro Ile Ser Gly Val Thr Arg Gln Gly Leu Asp Ala Leu Leu Asn
                    325                 330                 335

Ala Thr Ala Asp Leu Leu Glu Val Thr Pro Glu Phe Pro Leu Tyr Glu
                340                 345                 350

Glu Glu Leu Glu Glu Glu Thr Val His Tyr Gly Phe Asn Pro Glu Gly
                355                 360                 365

Pro Glu Phe Gln Ile Asp Arg Asp Ser Asp Ala Thr Trp Ile Leu Ser
            370                 375                 380

Gly Glu Lys Ile Glu Lys Leu Phe Gln Met Thr Asn Phe Asp His Asp
385                 390                 395                 400

Glu Thr Val Met Arg Phe Ala Arg Gln Leu Arg Gly Met Gly Val Asp
                    405                 410                 415

Glu Ala Leu Arg Ala Arg Gly Ala Lys Asp Gly Asp Leu Val Arg Ile
                420                 425                 430

Gly Glu Phe Glu Phe Glu Phe Val Glu
                435                 440

<210> SEQ ID NO 7
<211> LENGTH: 439
<212> TYPE: PRT
<213> ORGANISM: Streptococcus pyogenes

<400> SEQUENCE: 7

Glu Glu Ile Met Ser Met Phe Leu Asp Thr Ala Lys Ile Lys Val Lys
1               5                   10                  15

Ala Gly Asn Gly Gly Asp Gly Met Val Ala Phe Arg Arg Glu Lys Tyr
                20                  25                  30

Val Pro Asn Gly Gly Pro Trp Gly Gly Asp Gly Arg Gly Gly Asn
            35                  40                  45

Val Val Phe Val Val Asp Glu Gly Leu Arg Thr Leu Met Asp Phe Arg
    50                  55                  60

Tyr Asn Arg His Phe Lys Ala Asp Ser Gly Glu Lys Gly Met Thr Lys
65                  70                  75                  80

Gly Met His Gly Arg Gly Ala Glu Asp Leu Arg Val Arg Val Ser Gln
                85                  90                  95

Gly Thr Thr Val Arg Asp Ala Glu Thr Gly Lys Val Leu Thr Asp Leu
                100                 105                 110

Ile Lys His Gly Gln Glu Phe Ile Val Ala His Gly Gly Arg Gly Gly
            115                 120                 125

Arg Gly Asn Ile Arg Phe Ala Thr Pro Lys Asn Pro Ala Pro Glu Ile
        130                 135                 140

Ser Glu Asn Gly Glu Pro Gly Gln Glu Arg Glu Leu Gln Leu Glu Leu
145                 150                 155                 160
```

```
Lys Ile Leu Ala Asp Val Gly Leu Val Gly Phe Pro Ser Val Gly Lys
                165                 170                 175

Ser Thr Leu Leu Ser Val Ile Thr Ser Ala Lys Pro Lys Ile Gly Ala
            180                 185                 190

Tyr His Phe Thr Thr Ile Val Pro Asn Leu Gly Met Val Arg Thr Gln
        195                 200                 205

Ser Gly Glu Ser Phe Ala Val Ala Asp Leu Pro Gly Leu Ile Glu Gly
    210                 215                 220

Ala Ser Gln Gly Val Gly Leu Gly Thr Gln Phe Leu Arg His Ile Glu
225                 230                 235                 240

Arg Thr Arg Val Ile Leu His Ile Ile Asp Met Ser Ala Ser Glu Gly
                245                 250                 255

Arg Asp Pro Tyr Glu Asp Tyr Leu Ala Ile Asn Lys Glu Leu Glu Ser
            260                 265                 270

Tyr Asn Leu Arg Leu Met Glu Arg Pro Gln Ile Ile Val Ala Asn Lys
        275                 280                 285

Met Asp Met Pro Glu Ser Gln Glu Asn Leu Glu Glu Phe Lys Lys Lys
    290                 295                 300

Leu Ala Glu Asn Tyr Asp Glu Phe Glu Glu Leu Pro Ala Ile Phe Pro
305                 310                 315                 320

Ile Ser Gly Leu Thr Lys Gln Gly Leu Ala Thr Leu Leu Asp Ala Thr
                325                 330                 335

Ala Glu Leu Leu Asp Lys Thr Pro Glu Phe Leu Leu Tyr Asp Glu Ser
            340                 345                 350

Asp Met Glu Glu Glu Ala Tyr Tyr Gly Phe Asp Glu Glu Lys Ala
    355                 360                 365

Phe Glu Ile Ser Arg Asp Asp Ala Thr Trp Val Leu Ser Gly Glu
370                 375                 380

Lys Leu Met Lys Leu Phe Asn Met Thr Asn Phe Asp Arg Asp Glu Ser
385                 390                 395                 400

Val Met Lys Phe Ala Arg Gln Leu Arg Gly Met Gly Val Asp Glu Ala
                405                 410                 415

Leu Arg Ala Arg Gly Ala Lys Asp Gly Asp Leu Val Arg Ile Gly Lys
            420                 425                 430

Phe Glu Phe Glu Phe Val Asp
            435

<210> SEQ ID NO 8
<211> LENGTH: 428
<212> TYPE: PRT
<213> ORGANISM: Bacillus subtilis

<400> SEQUENCE: 8

Met Phe Val Asp Gln Val Lys Val Tyr Val Lys Gly Gly Asp Gly Gly
1               5                   10                  15

Asn Gly Met Val Ala Phe Arg Arg Glu Lys Tyr Val Pro Lys Gly Gly
            20                  25                  30

Pro Ala Gly Gly Asp Gly Gly Lys Gly Gly Asp Val Phe Glu Val
        35                  40                  45

Asp Glu Gly Leu Arg Thr Leu Met Asp Phe Arg Tyr Lys Lys His Phe
    50                  55                  60

Lys Ala Ile Arg Gly Glu His Gly Met Ser Lys Asn Gln His Gly Arg
65                  70                  75                  80

Asn Ala Asp Asp Met Val Ile Lys Val Pro Pro Gly Thr Val Val Thr
                85                  90                  95
```

Asp Asp Asp Thr Lys Gln Val Ile Ala Asp Leu Thr Glu His Gly Gln
            100                 105                 110
Arg Ala Val Ile Ala Arg Gly Gly Arg Gly Arg Gly Asn Ser Arg
        115                 120                 125
Phe Ala Thr Pro Ala Asn Pro Ala Pro Gln Leu Ser Glu Asn Gly Glu
        130                 135                 140
Pro Gly Lys Glu Arg Tyr Ile Val Leu Glu Leu Lys Val Leu Ala Asp
145                 150                 155                 160
Val Gly Leu Val Gly Phe Pro Ser Val Gly Lys Ser Thr Leu Leu Ser
                165                 170                 175
Val Val Ser Ser Ala Lys Pro Lys Ile Ala Asp Tyr His Phe Thr Thr
            180                 185                 190
Leu Val Pro Asn Leu Gly Met Val Glu Thr Asp Asp Gly Arg Ser Phe
        195                 200                 205
Val Met Ala Asp Leu Pro Gly Leu Ile Glu Gly Ala His Gln Gly Val
        210                 215                 220
Gly Leu Gly His Gln Phe Leu Arg His Ile Glu Arg Thr Arg Val Ile
225                 230                 235                 240
Val His Val Ile Asp Met Ser Gly Leu Glu Gly Arg Asp Pro Tyr Asp
                245                 250                 255
Asp Tyr Leu Thr Ile Asn Gln Glu Leu Ser Glu Tyr Asn Leu Arg Leu
            260                 265                 270
Thr Glu Arg Pro Gln Ile Ile Val Ala Asn Lys Met Asp Met Pro Glu
        275                 280                 285
Ala Ala Glu Asn Leu Glu Ala Phe Lys Glu Lys Leu Thr Asp Asp Tyr
        290                 295                 300
Pro Val Phe Pro Ile Ser Ala Val Thr Arg Glu Gly Leu Arg Glu Leu
305                 310                 315                 320
Leu Phe Glu Val Ala Asn Gln Leu Glu Asn Thr Pro Glu Phe Pro Leu
                325                 330                 335
Tyr Asp Glu Glu Glu Leu Thr Gln Asn Arg Val Met Tyr Thr Met Glu
            340                 345                 350
Asn Glu Glu Val Pro Phe Asn Ile Thr Arg Asp Pro Asp Gly Val Phe
        355                 360                 365
Val Leu Ser Gly Asp Ser Leu Glu Arg Leu Phe Lys Met Thr Asp Phe
370                 375                 380
Ser Arg Asp Glu Ser Val Lys Arg Phe Ala Arg Gln Met Arg Gly Met
385                 390                 395                 400
Gly Val Asp Glu Ala Leu Arg Glu Arg Gly Ala Lys Asp Gly Asp Ile
                405                 410                 415
Ile Arg Leu Leu Glu Phe Glu Phe Glu Phe Ile Asp
            420                 425

<210> SEQ ID NO 9
<211> LENGTH: 424
<212> TYPE: PRT
<213> ORGANISM: Clostridium acetobutylicum

<400> SEQUENCE: 9

Met Phe Val Asp Lys Ala Arg Ile Phe Val Lys Ser Gly Asp Gly Gly
1               5                   10                  15
Asp Gly Ala Val Ser Phe Arg Arg Glu Lys Tyr Ile Pro Leu Gly Gly
            20                  25                  30
Pro Asp Gly Gly Asp Gly Gly Glu Gly Gly Asp Val Ile Leu Val Val

```
              35                  40                  45
Asp Pro Asn Met Thr Thr Leu Leu Asp Phe Lys Tyr Lys Arg Lys Tyr
     50                  55                  60

Val Ser Glu Arg Gly Gln Asn Gly Gln Gly Ala Lys Cys Tyr Gly Arg
 65                  70                  75                  80

Asp Gly Lys Asp Leu Tyr Ile Lys Val Pro Met Gly Thr Ile Ile Arg
                 85                  90                  95

Asp Val Glu Thr Asp Lys Ile Met Ala Asp Leu Ala His Lys Asp Asp
                100                 105                 110

Lys Phe Val Ile Val Lys Gly Arg Gly Lys Gly Asn Val Lys
                115                 120                 125

Phe Cys Thr Pro Thr Arg Gln Ala Pro Asn Phe Ala Gln Pro Gly Met
    130                 135                 140

Pro Gly Glu Glu Arg Trp Ile Ser Leu Glu Leu Lys Leu Leu Ala Asp
145                 150                 155                 160

Val Gly Leu Ile Gly Phe Pro Asn Val Gly Lys Ser Thr Leu Leu Ser
                165                 170                 175

Val Ala Ser Lys Ala Arg Pro Lys Ile Ala Lys Tyr His Phe Thr Thr
                180                 185                 190

Ile Thr Pro Asn Leu Gly Val Val Asp Val Ser Gly Ile Ser Ser Phe
            195                 200                 205

Val Met Ala Asp Ile Pro Gly Ile Ile Glu Gly Ala Ser Glu Gly Val
    210                 215                 220

Gly Leu Gly Phe Glu Phe Leu Arg His Ile Glu Arg Thr Arg Leu Leu
225                 230                 235                 240

Val His Val Val Asp Ile Ser Gly Ser Glu Gly Arg Asp Pro Leu Glu
                245                 250                 255

Asp Phe Leu Lys Ile Asn Glu Glu Leu Lys Lys Tyr Asn Ile Lys Leu
            260                 265                 270

Trp Asp Arg Pro Gln Ile Val Ala Ala Asn Lys Ala Asp Met Val Tyr
    275                 280                 285

Asp Asp Asp Gln Phe Asn Lys Phe Arg Glu Glu Leu Asn Lys Leu Gly
    290                 295                 300

Tyr Lys Asn Val Phe Lys Ile Ser Ala Ala Thr Arg Met Gly Val Glu
305                 310                 315                 320

Asp Leu Leu Lys Glu Cys Ala Arg Val Leu Ser Thr Ile Pro Val Thr
                325                 330                 335

Asp Met Glu Ile Pro Glu Glu Glu Arg Phe Val Pro Glu Asp Lys His
            340                 345                 350

Phe Thr Tyr Thr Ile Arg Lys Glu Gly Asp Thr Tyr Ile Val Glu Gly
    355                 360                 365

Thr Phe Val Asp Arg Leu Leu Ala Ser Val Asn Val Asn Glu Pro Asp
370                 375                 380

Ser Phe Arg Tyr Phe His Lys Val Leu Arg Asn Lys Gly Val Met Ala
385                 390                 395                 400

Glu Leu Glu Glu Met Gly Ile Lys Asp Gly Asp Met Val Arg Leu Asn
                405                 410                 415

Asp Phe Glu Phe Glu Phe Leu Lys
            420

<210> SEQ ID NO 10
<211> LENGTH: 26
<212> TYPE: DNA
<213> ORGANISM: Staphylococcus aureus
```

```
<400> SEQUENCE: 10
cgccatatgt ttgtggatca agtcaa                                           26

<210> SEQ ID NO 11
<211> LENGTH: 30
<212> TYPE: DNA
<213> ORGANISM: Staphylococcus aureus

<400> SEQUENCE: 11
ccgctcgagt tattcaacga attcaaattc                                       30
```

STAPHYLOCOCCAL GTPASE OBG NUCLEOTIDE SEQUENCE ENCODING STAPHYLOCOCCAL GTP-BINDING PROTEIN

CROSS-REFERENCE TO RELATED APPLICATIONS

This application claims the benefit of U.S. Provisional Application No. 60/184,742, filed Feb. 24, 2000.

FIELD OF THE INVENTION

The present invention generally relates to nucleotide sequences that encode proteins which are essential for bacterial growth. More particularly, the present invention is directed to a GTPase obg gene encoding a GTP-binding protein in Staphylococcal bacterial strains. Specifically, the present invention is directed to a Staphylococcus aureus ("S. aureus") obg gene that is capable of expression in a host cell to produce enzymatically functional S. aureus GTP-binding protein. Additionally, the present invention pertains to recombinant expression vectors incorporating the GTPase obg gene of the present invention. The present invention is further directed to Staphylococcal GTP-binding protein, methods for producing GTP-binding protein, and methods for using GTP-binding protein as a novel thereapeutic target in affinity-based pharmacological screening procedures for the discovery of antibiotics active against S. aureus and other Staphylococcal bacteria.

BACKGROUND OF THE INVENTION

Numerous pathogenic organisms are responsible for infectious disease and health-related problems in humans and other animals throughout the United States and the world. As treatments are developed for combating a particular organism, such as treatments incorporating newly developed antibiotics and chemical compounds effective at eliminating existing strains of a particular organism, newer strains of such organisms emerge which are resistant to the existing treatments. Accordingly, there remains a continual need for the development of new ways for pharmaceutically combating pathogenic organisms.

One particular organism of concern is the bacterium S. aureus, which is an opportunistic human pathogen both in the community and in hospitals, and is the primary cause of nosocomial bacterial infections in the United States. S. aureus has a highly invasive nature and is associated with a number of life threatening systemic illnesses, such as bacteremia/sepsis, toxic shock syndrome and toxic epidermal necrolysis, as well as common bacterial infections of the skin. Once the organism enters the bloodstream, patients are at risk of developing serious diseases such as endocarditis, osteomyelitis, and septic shock.

Despite the development and use of newer antimicrobial agents to combat S. aureus infections, the morbidity and mortality from serious S. aureus infections remain high. One reason is that S. aureus is adept in developing resistance to multiple antibiotics. The recent emergence of methicillin-resistant and vancomycin-resistant strains of S. aureus in Japan, and subsequently in the United States, has further highlighted the importance of finding alternative approaches to the prevention and treatment of Staphylococcal infections, and has focused renewed attention on the need for development of new classes of antibiotics to combat such bacterial strains. Despite the imminent crisis in S. aureus antibiotic resistance, the identification of novel targets for the development of novel antimicrobial agents remains elusive.

One promising way of pharmaceutically combating bacterial strains, including S. aureus and other Staphylococcal strains, is to interfere with genetic processes relating to growth and/or viability of the bacteria. Methods for combating organisms by interfering with genetic processes essential to survival and growth of the organism are becoming of increasing interest. In particular, researchers are directing their attention to chemical compounds that interfere with such processes.

A potential target for use with screening processes to identify chemical compounds that are useful in combating pathogenic organisms is a GTPase superfamily of GTP (guanosinetriphosphate)-binding proteins that includes G-proteins, elongation factors in E. coli, mammalian Ras, and procaryotic proteins such as Era, FtsZ, and Fth, etc. These GTPase regulatory molecules are classified as belonging to the GTPase superfamily due to a common ability to bind guanine nucleotides and hydrolyse GTP. March, "Membrane-Associated GTPases in Bacteria", Molec. Microbiol., Vol. 6, pp. 1253–57, 1992.

GTP-binding proteins are important signaling molecules in bacteria as well as in eukaryotic cells. GTP-binding proteins have been recognized for many years as components of signal transduction pathways in eukaryotes. Only recently, however, has it been discovered that prokaryotes contain GTP-binding proteins that are essential for growth and/or viability of the organism. The involvement of these bacterial proteins in signal transduction in prokaryotes, however, is still not entirely clear.

One member of this superfamily of GTP-binding proteins which is of particular interest is the protein expressed by the obg gene (short for spoOB-associated GTP-binding protein). The obg gene specifically encodes a GTP-binding protein which is essential for bacterial growth and which is structurally conserved across an extraordinarily wide range of bacterial species. Obg was initially identified as a gene dowstream of the stage 0 sporulation gene spoOB in Bacillus subtilis in 1989. Trach et al., "The Bacillus subtilis spoOB Stage 0 Sporulation Operon Encodes An Essential GTP-Binding Protein" J. Bacteriol., Vol. 171, pp. 1362–71, 1989. Transcription analysis of this operon revealed that spoOB and obg are cotranscribed.

Various observations have been made about the Obg protein in certain organisms. Obg in Bacillus subtilis has been shown to bind GTP by the cross-linking method. Trach et al., supra. Bacillus subtilis Obg has also been characterized by its enzymatic activity with respect to GTP hydrolysis. Welsh et al., "Biochemical Characterization of the Essential GTP-Binding Protein Obg of Bacillus subtilis", J. Bacteriol., Vol. 176, pp. 7161–68, 1994. It has also been demonstrated that Obg plays a crucial role in sporulation induction in Bacillus subtilis and Streptomyces griseus. Kok et al., "Effects on Bacillus subtilis of a Conditional Lethal Mutation in the Essential GTP-Binding Protein Obg", J. Bacteriol., Vol. 176, pp. 7155–60, 1994; Okamoto et al., "Molecular Cloning and Characterization of the obg Gene of Streptomyces griseus in Relation to the Onset of Morphological Differentiation", J. Bacteriol., Vol. 179, pp. 170–79, 1997.

Very little is known, however, about the physiological function of Obg. Obg homologs have recently been discovered in a diverse range of organisms ranging from bacteria to archaea to humans, and the evolutionary conservation between distantly related species suggests that this family of GTP-binding proteins has a fundamental, but unknown, cellular function. It has been proposed that, by monitoring the intracellular GTP pool size, Obg is involved in sensing changes in the nutritional environment leading ultimately to morphological differentiation. Okamoto et al., supra.

Obg is a unique GTPase in that it possesses an extended N-terminal glycine-rich domain not found in eukaryotic or archaeal homologs. An isolated *Bacillus subtilus* temperature-sensitive obg mutant was found to carry two closely linked missense mutations in the N-terminal domain, suggesting that this portion of obg is essential for cellular function. Kok et al., supra.

Very little is known about the essential functions of Obg, however. To date, Obg has been validated to be essential for growth in both Gram-negative bacteria (*E. coli, Caulobacter crescentus*) and Gram-positive bacteria (*Bacillus subtilis*). Maddock et al., "Identification of an Essential *Caulobacter crescentus* Gene Encoding a Member of the Obg Family of GTP-Binding Proteins", J. Bacteriol., Vol. 179, pp. 6426–31, 1997; Arigoni et al., "A Genome-Based Approach for the Identification of Essential Bacterial Genes", Nature Biotechnology, Vol. 16, pp. 851–56, 1998; Trach et al., supra. In addition, depletion of Obg has been shown to cause cessation of *Bacillus subtilis* cell growth. Vidwans et al., "Possible Role for the Essential GTP-Binding Protein Obg in Regulating the Initiation of Sporulation in *Bacillus subtilis*", J. Bacteriol., Vol. 177, pp. 3308–11, 1995. Because the Obg protein appears to be essential for cell growth and/or viability, compounds that interfere with Obg functionality, such as compounds which bind with and inhibit Obg, are of interest as potential antimicrobial agents.

The Obg family is attractive as a potential target for antibacterial drug discovery for several reasons. First, the obg gene is a novel target because it is a hypothetical open reading frame (ORF) and its function is essentially unknown. Further, Obg homologs are highly conserved among bacteria. Additionally, there is a low toxicity potential because the obg gene is distinguishable from its nearest human homologs. Furthermore, the obg gene encodes essential cell function, to the extent that mutation is detrimental for cell growth. Finally, Obg protein GTPase activity can be assayed in vitro, in light of functional similarity with in vivo activity, and assays are relatively simple for target development.

U.S. Pat. Nos. 5,585,277 and 5,679,582 to Bowie et al. disclose methods for screening chemical compounds for potential pharmaceutical or antimicrobial effectiveness. Among other things, these patents teach methods for identifying possible ligands which bind to target proteins. The methods of these patents may be useful in affinity-based assays for the initial identification of chemical compounds that interfere in vitro with protein function by binding with and inhibiting the protein of interest.

To date, however, the obg gene sequence and the encoded protein have not been identified in Staphylococcal bacterial strains, such as *S. aureus*. Accordingly, it can be seen that there remains a need in the art for the identification of GTPase obg gene DNA sequences that encode GTP-binding protein in Staphylococcal bacterial strains, such as *S. aureus*. Further, there remains a need in the art for the identification of a Staphylococcal obg gene that is capable of expression in a host cell to produce functional Staphylococcal GTP-binding protein for use in screening procedures for antimicrobial compounds. Additionally, there remains a need for recombinant expression vectors incorporating a Staphylococcal GTPase obg gene. Further, there remains a need for methods for producing GTP-binding protein and for using GTP-binding protein as a novel therapeutic target in screening procedures directed toward the discovery of antimicrobial agents active against Staphylococcal bacteria, and *S. aureus* in particular. The present invention is directed to meeting these needs.

SUMMARY OF THE INVENTION

It is an object of the present invention to provide a new and useful nucleotide sequence encoding Staphylococcal GTP-binding protein.

It is another object of the present invention to provide a Staphylococcal GTPase obg gene sequence.

It is a further object of the present invention to provide a novel *S. aureus* GTPase obg DNA sequence It is yet another object of the present invention to provide a Staphylococcal GTPase Obg protein for use with antimicrobial compound screening methods.

A still further object is to provide a *S. aureus* GTP-binding protein amino acid sequence for use as a novel therapeutic target in affinity-based pharmacological screening procedures.

Yet another object of the present invention is to provide recombinant expression vectors incorporating the Staphylococcal GTPase obg gene of the present invention.

Still a further object of the present invention is to provide recombinant expression vectors that are useful in host cells, such as *E. coli*, for producing Staphylococcal GTP-binding protein.

It is still a further object of the present invention to provide methods for producing Staphylococcal GTP-binding protein that is functional in in vitro assays for identifying antimicrobial compounds active against Staphylococcal bacteria.

It is yet another object of the present invention to provide methods for using GTP-binding protein in affinity-based screening procedures for the identification of antimicrobial agents effective against Staphylococcal bacteria such as *S. aureus*.

According to the present invention, an isolated polynucleotide that encodes a Staphylococcal GTP-binding protein is provided. More particularly, the polynucleotide encodes a *Staphylococcus aureus* GTP-binding protein. The isolated polynucleotide may particularly comprise a nucleotide sequence as set forth in SEQ ID NO:1, and may encode a polypeptide comprising an amino acid sequence as set forth in SEQ ID NO:2. The isolated polynucleotide may comprise a Staphylococcal, and particularly a *Staphylococcus aureus*, GTPase obg gene. Variations of polynucleotides are contemplated, such as those comprising a complementary DNA strand, or which encode a fragment, derivative or analog of the polypeptide.

The present invention is also directed to an isolated and purified polypeptide comprising a Staphylococcal GTP-binding protein, and particularly a *Staphylococcus aureus* GTP-binding protein, such as a polypeptide encoded by an obg gene. In particular, the polypeptide may comprise an amino acid sequence as set forth in SEQ ID NO:2. The polypeptide may alternatively be a fragment, derivative or analog of a polypeptide.

The present invention additionally provides a recombinant expression vector comprising a polynucleotide that encodes a Staphylococcal GTP-binding protein, which may particularly be a *Staphylococcus aureus* GTP-binding protein. The expression vector may be a plasmid, and specifically a pET14b plasmid.

The present invention additionally pertains to an engineered host cell for use in producing Staphylococcal GTP-binding protein. The engineered host cell comprises an isolated polynucleotide that encodes a Staphylococcal GTP-binding protein, and particularly Staphylococcus aureus GTP-binding protein. The host cell may specifically be an E. coli bacterial cell, and the isolated polynucleotide may be introduced into the host cell by a vector, which may further include a regulatory sequence operatively linked to the isolated polynucleotide, such that expression of the isolated polynucleotide may be induced by addition of an inducing agent appropriate to the regulatory sequence.

The present invention further relates to a method of producing Staphylococcal GTP-binding protein, such as Staphylococcus aureus GTP-binding protein. The method broadly comprises the steps of introducing into suitable host cells a polynucleotide that encodes Staphylococcal GTP-binding protein, and culturing the host cells under conditions in which the host cells express the polynucleotide to produce Staphylococcal GTP-binding protein. The method may include the further step of recovering the Staphylococcal GTP-binding protein. The polynucleotide may be introduced into the host cells with a suitable expression vector, such as a plasmid. The host cells are preferably E. coli bacterial cells, such as E. coli BL21 (DE3).pLys.S cells. The method may include contacting the host cells with an inducing agent, such as isopropylthiogalactoside (IPTG), thereby to induce expression of the polynucleotide.

Finally, the present invention provides a method for high throughput screening to identify potential antimicrobial compounds useful against Staphylococcal bacterial strains. The steps of this method include providing a selected amount of Staphylococcal GTP-binding protein, contacting the Staphylococcal GTP-binding protein with a test compound to form a test combination, and determining whether the test compound binds with the Staphylococcal GTP-binding protein. A test compound that binds with the Staphylococcal GTP-binding protein is identified as a potential antimicrobial compound useful against Staphylococcal bacterial strains. The Staphylococcal GTP-binding protein may be a polypeptide having the sequence set forth in SEQ ID NO:2, or may be a fragment, derivative or analog thereof. The step of determining whether the test compound binds with the Staphylococcal GTP-binding protein may be accomplished by the steps of providing a control group of Staphylococcal GTP-binding protein, subjecting the test combination and control group to increasing temperature, and measuring the temperature at which biophysical catalyzation unfolding of the Staphylococcal GTP-binding protein occurs in each of the test combination and the control group. When unfolding of the Staphylococcal GTP-binding protein in the test combination occurs at a higher temperature than unfolding of the Staphylococcal GTP-binding protein in the control group, the test compound is, identified as a compound that binds with Staphylococcal GTP-binding protein.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

FIG. 1 shows the nucleotide and deduced amino acid sequences (SEQ ID NO:1 and SEQ ID NO:2, respectively) of the S. aureus obg gene identified by the present invention;

FIG. 2 is a graphical illustration comparing the alignment of the inferred amino acid sequence (SEQ ID NO:2) of the S. aureus obg gene fragment identified by the present invention relative to corresponding regions of various bacterial strains (SEQ ID NO:5–SEQ ID NO:9);

FIG. 3 is a diagrammatic illustration of the unrooted phylogenetic tree for Obg amino acid sequences for various species, including the Obg protein of S. aureus identified by the present invention;

FIG. 4A is a photographic illustration of an SDS-polyacrylamide gel electropherogram depicting total soluble proteins and purified Obg proteins from E. coli overexpression of recombinant S. aureus Obg according to the present invention;

FIG. 4B is a photographic illustration of Western blots showing the reactions of anti-His-Tag antibody and anti-Caulobacter Obg antibody to the purified Obg protein of the present invention.

DETAILED DESCRIPTION OF THE EXEMPLARY EMBODIMENTS

Figure 5:
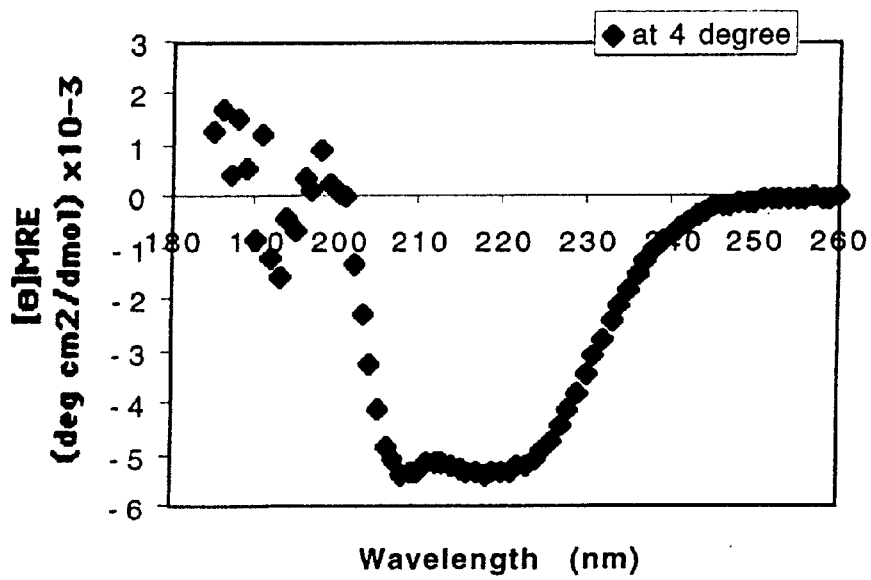
FIG. 5 shows the far UV CD spectra of purified bacterially expressed S. aureus Obg protein according to the present invention.

The present invention concerns the isolation and purification of the obg gene from Staphylococcal bacterial strains, and particularly from an important pathogenic bacterium, Staphylococcus aureus ("S. aureus"). The present invention also concerns engineered expression of Staphylococcal (and particularly S. aureus) Obg protein in a host cell, such as E. coli. Additionally, the present invention concerns the use of Obg protein in high-throughput screening to identify potential antimicrobial agents active against Staphylococcal bacterial strains as inhibitors of Obg function.

I. DNA Sequencing and Analysis of the S. aureus obg Gene

A. Cloning and Sequencing of the obg Gene from S. aureus

A DNA fragment expected to include the full-length obg gene was isolated and amplified from S. aureus by polymerase chain reaction (PCR). The PCR process used degenerate oligonucleotides derived from conserved amino acid segments of known obg homologs from other bacteria (MFVDQVK and EFEFID; amino acid 1–7 and 423–428, respectively, of the Bacillus subtilis obg). In particular, the oligonucleotide primers used had the following nucleotide sequences:

(1) 5'-CGCCATATGTTYGTNGAYCARGTNAA-3' (SEQ ID NO:3)

(2) 5'-CCGCTCGAGTTATTCNACRAAYTCRAAYTC-3' (SEQ ID NO:4)

To confirm that the resulting PCR amplified S. aureus DNA contained obg, the nucleotide sequence of the entire fragment was determined. Plasmid templates for nucleotide sequencing were purified using Qiagen miniprep kits, manufactured by Qiagen, located in Valencia, Calif. PCR cycle sequencing was carried out with an APPlied Biosystems automated sequencer, at the Massachusetts General Hospital DNA Sequencing Core Facility, Department of Molecular Biology, Boston, Mass. The S. aureus obg nucleotide sequence encodes a 1290 base pair (bp) open reading frame (ORF) which has an overall G+C composition of 36.6% as illustrated in FIG. 1 and as set forth as SEQ ID NO:1. The putative start and stop codons are underlined in FIG. 1.

The deduced amino acid sequence of the PCR product showed significant homology to obg from other bacteria, suggesting that the PCR product comprised S. aureus obg. The ORF encodes a polypeptide of 430 amino acids long with a predicted molecular mass of 45.8 kDa. The amino acid sequence of this polypeptide is set forth as SEQ ID NO:2. The *S. aureus* Obg is an acidic protein with an estimated pI value of 4.9.

The alignment of the inferred amino acid sequence (SEQ ID NO:2) of the *S. aureus* obg gene of the present invention is illustrated in FIG. 2 along with corresponding regions of *Enterococcus faecalis* (SEQ ID NO: 5), *Enterococcus faecium* (SEQ ID NO: 6), *Streptococcus pyogenes* (SEQ ID NO: 7), *Bacillus subtilis* (SEQ ID NO: 8), and *Clostridium acetobutylicum* (SEQ ID NO: 9). The consensus GTP-binding motifs are indicated by overlying bars. Analysis of the amino acid sequence shows that key structural elements are highly conserved in the inferred amino acid sequence of *S. aureus* Obg, as seen in FIG. 2. Amino acid residues in the N-terminal region are particularly well conserved compared to Obg from other bacterial species, while those in the C-terminal side are far less conserved. Consistent with other GTP-binding proteins, *S. aureus* Obg protein possesses three consensus sequence motifs (FIG. 2) which confer GTP-binding activity.

B. Phylogenetic Analysis of *S. aureus* obg

Referring to FIG. 3, a more in-depth evolutionary examination of the *S. aureus* Obg was carried out using the PHYLIP phylogenetic analysis package. Felsenstein, "Phylogenetic Inference Program (PHYLIP) Manual Version 3.5c", University of Washington, Seattle, 1993. FIG. 3 shows the unrooted tree for obg amino acid sequences analyzed by using the PROTDIST and FITCH programs from the PHYLIP phylogenetic package: Abbreviated species are as follows:

A. thaliana=*Arabidopsis thaliana*;
H. influenza=*Haemophilus influenza*;
E. coli=*Escherichia coli*;
C. trachomatis=*Chlamydia trachomatis*;
M. tuberculosis=*Mycobacterium tuberculosis*;
C. acetobutylicum=*Clostridium acetobutylicum*;
S. aureus=*Staphylococcus aureus*;
E. faecium=*Enterococcus faecium*;
S. pyogenes=*Streptococcus pyogenes*;
B. subtilis=*Bacillus subtilis*;
H. pylon=*Helicobacter pylon*;
M. pneumonia=*Mycoplasma pneumonia*; and
C. crescentus=*Caulobacter crescentus*. Amino acid sequences obtained from the combined GenBank/Swissprot/PIR database were used in the phylogenetic analyses, instead of DNA sequences, to eliminate biases due to different G+C ratios. Normand et al., "Nucleotide Sequence of nifD from Frankia alni Strain ARI3: Phylogenetic Inference", Mol. Biol. Evol., Vol. 9, pp. 495–506, 1992. Sequences were aligned using ClustalW. Swofford et al., "Phylogenetic Inference", Molecular Systematics, Sinauer Associates, Inc., pp. 407–514, 1996. The PHYLIP 3.5c phylogenetic inference software package, in the form of compiled executable programs for Macintosh computers, was used for comparison of the protein sequences.

The primary sequence analysis was carried out using the PROTDIST program using a Dayhoff amino acid comparison matrix, manufactured by Dayhoff. This program produced distances expressed in expected changes per amino acid position, including back mutations. The distance matrices produced were converted to phylogenetic trees using the FITCH program which uses the Fitch-Margoliash least-squares distance matrix. TREEDRAW was used to generate the unrooted phylogenetic trees presented.

As shown in the unrooted phylogenetic tree, Obg is highly conserved among a wide range of bacterial species. Notably, *S. aureus* Obg forms a distinct cluster with other Gram-positive bacteria, while the closest homolog in humans is only distantly related to bacterially-derived proteins.

C. Polynucleotides Encoding Staphylococcal GTP-binding Protein

The present invention provides an isolated nucleic acid (polynucleotide) having the nucleotide sequence as set forth in SEQ ID NO:1, which encodes for the polypeptide having the deduced amino acid sequence as set forth in SEQ ID NO:2. Additionally, it should be understood that the present invention generally contemplates polynucleotides encoding Staphylococcal GTP-binding protein, as well as polynucleotides specifically encoding the *S. aureus* GTP-binding protein.

It should be understood that polynucleotides according to the present invention may be in the form of RNA or in the form of DNA, including cDNA, genomic DNA, and synthetic DNA. The DNA may be double-stranded or single-stranded. If single stranded, the DNA may be the coding strand or non-coding (anti-sense) strand. The coding sequence which encodes the polypeptide may be identical to the coding sequence as set forth in SEQ ID NO:1 or may be a different coding sequence which, as a result of the redundancy or degeneracy of the genetic code, encodes the same polypeptide as does the polynucleotide set forth in SEQ ID NO:1.

The polynucleotide that encodes the polypeptide as set forth in SEQ ID NO:2 may include, without limitation: (a) only the coding sequence for the polypeptide; (b) the coding sequence for the polypeptide and additional coding sequence (s) such as a leader sequence; and (c) the coding sequence for the polypeptide, optionally including additional coding sequence(s), and further including non-coding sequence(s), such as introns. Accordingly, it should be understood that polynucleotides according to the present invention may include only coding sequence for the polypeptide, or may include additional coding and/or non-coding sequences.

The present invention further contemplates variations of the herein described polynucleotides that encode for fragments, analogs and derivatives of the polypeptide having the deduced amino acid sequence as set forth in SEQ ID NO:2. A "fragment", "derivative" or "analog" of the polypeptide should be understood to encompass a polypeptide which retains essentially the same biological function or activity as such polypeptide. These polynucleotide variations may be naturally occurring allelic variants of the polynucleotide or nonnaturally occurring variants of the polynucleotide, and include deletion variants, substitution variants and addition or insertion variants. An allelic variant should be understood to mean an alternate form of a polynucleotide sequence which may have a substitution, deletion or addition of one or more nucleotides, which does not substantially alter the function of the encoded polypeptide.

II. Construction, Expression and Purification of Enzymatically Active *S. aureus* Obg GTP-binding Protein.

The present invention additionally relates to the GTP-binding protein encoded by the obg gene in Staphylococcal bacterial strains, and *S. aureus* in particular. Additionally, the present invention is directed to expression vectors, host cells and methods for producing the GTP-binding protein using such expression vectors and host cells. In particular, the obg gene from the Gram-positive pathogenic bacterium, *S. aureus*, was expressed in *E. coli*. Purified *S. aureus* Obg protein recovered therefrom showed enzymatic activity in vitro and its far ultraviolet circular dichroism spectra suggested alpha-helical secondary structure, consistent with Obg.

A. Construction of a Suitable Expression Vector and Host Cell

A 1290 bp DNA fragment encoding the *S. aureus* obg gene was amplified by PCR using the following oligonucleotide primers:

(1) 5'-CGC(CATATG)TTTGTGGATCAAGTCAA-3' (SEQ ID NO:1 0)

(2) 5'-CCG(CTCGAG)TTATTCAACGAATTCAAATTC-3' (SEQ ID NO: 11)

The *S. aureus* obg coding sequence was cloned into vector pET14b for high-level expression in *E. coli* (Novagen, Madison, Wis.). Here, the isolated and amplified PCR product was digested with NdeI and BamHI (restriction sites are shown in parentheses in the above primers), ligated into the expression vector pET14b (Novagen) and transformed into *E. coli* BL21 (DE3).pLys.S. Recombinant Obg contained an additional twenty amino acid residues: six histidines for rapid affinity purification purposes and a thrombin cleavage site to remove extra N-terminal sequences if so required (recombinant 6× his-tagged Obg was therefore 49,368 Da). The resulting construct specified an N-terminal 6×his-tag fused to the entire Obg coding region.

It should be understood that, in addition to the particular example above, the present invention contemplates various vectors that include polynucleotides of the present invention, host cells which are genetically engineered with vectors of the invention and the production of polypeptides of the invention by recombinant techniques.

The present invention generally contemplates that host cells, such as *E. coli*, may be genetically engineered (transduced or transformed or transfected) with the vectors of this invention which may be, for example, expression vectors or integrative vectors. It should be understood that the polynucleotide may be included in any one of a variety of expression vectors for expressing a polypeptide. The vectors contemplated by the present invention may be, for example, in the form of plasmids, viral particles, phages, etc. It should be appreciated that any form of vector may be used provided that it is replicable and viable in the host. The engineered host cells can be cultured in conventional nutrient media, where the culture conditions, such as temperature, pH and the like, are those generally known for culturing the host cell selected for expression, as apparent to the ordinarily skilled artisan.

The appropriate DNA sequence may be inserted into the vector by a variety of procedures as known in the art. In general, the DNA sequence is inserted into an appropriate restriction endonuclease site(s) by procedures as understood by those ordinarily skilled in the art. It is preferred that the DNA sequence in the expression vector is operatively linked to an appropriate control sequence, such as a promoter sequence, such that expression of the DNA sequence may be induced upon addition of an appropriate inducing agent, such as IPTG in the case of the pET14b plasmid vector. The expression vector thus formed may be employed to transform an appropriate host with the DNA sequence of interest, thereby to permit the host to overexpress the protein upon addition of suitable quantities of the inducing agent.

The present invention is also directed to host cells containing the polynucleotide sequence of the present invention, such as host cells into which the polynucleotide sequence has been introduced, such as by an expression vector as described above. Various types of host cells are contemplated, such as prokaryotic cells, bacterial cells, lower eukaryotic cells such as yeast cells, and higher eukaryotic cells such as mammalian cells. It should further be understood that the expressed polypeptides of the present invention may be recovered from the host cells by conventional techniques as known in the art.

B. Expression and Purification of GTP-binding Protein

Here, protein expression was induced by adding IPTG (final concentration 1 mM) to a growing culture (30° C.) at OD600=0.7. Three hours after induction, the cells were harvested, resuspended in binding buffer (5 mM imidazole, 0.5 M NaCl, 20 mM Tris-HCl, pH 7.9) and sonicated on ice. Cell debris was removed by centrifugation at 15,000 rpm for 15 minutes, and the clarified supernatant was purified on an $Ni^{++}$ affinity column manufactured by Novagen, according to the manufacturer's instructions. Here, soluble recombinant Obg was purified by $Ni^{++}$ affinity chromatography to produce a protein of high purity (FIG. 4A, lanes 4 & 5) which was used in preliminary GTPase assays. The yield per liter of culture of the purified protein was approximately 5 mg. The protein eluted from the column with the following buffer, 1 M imidazole, 0.5 M NaCl, 20 mM Tris-HCl, pH 7.9, was essentially homogeneous.

As shown in FIG. 4A, the *E. coli* BL21 (DE3).pLys.S containing the pET-Obg construct expressed a soluble protein with an apparent molecular size of 55 kDa. This value is higher than the molecular weight calculated from the protein's primary sequence. The difference may be due to an imperfect spherical shape or presence of highly charged amino acids. FIG. 4A illustrates SDS-PAGE showing total soluble proteins and purified Obg proteins, where the size of the Obg protein is indicated by an arrow. Lane 1 shows molecular weight standards (SeeBlue, Novex): 250, 98, 64, 50, 36 kDa; lane 2 shows extract prepared from cells harboring vector pET14b alone; lane 3 shows extract prepared from cells containing pET14b vector with the obg gene; and lanes 4 and 5 show purified Obg protein. As illustrated in FIG. 4A, recombinant Obg was not detectable either in extract from cells not treated with IPTG nor in cells harboring vector pET14b alone (FIG. 4A, lane 2).

The identity of the overexpressed protein as Obg was confirmed by Western blots using anti-6×his antibody as well as polyclonal anti-Caulobacter Obg antibody. Western blots are illustrated in FIG. 4B, showing the reactions of anti-His-Tag antibody (Novagen) and anti-Caulobacter Obg antibody to the purified Obg protein. Here, purified *S. aureus* Obg was resolved by SDS-PAGE and transferred to a PVDF membrane. The membrane was incubated overnight in TBST buffer (50 mM Tris/HCl, 150 mM NaCl, 0.1% (v/v) Tween 20, pH 7.5) containing 5% (w/v) BSA. After blocking, the membranes were incubated with anti-6×his-antibody or anti-Caulobacter Obg antibody (diluted 1:1000 in TBST buffer) for 30 min, washed with TBST buffer and incubated with gentle shaking at room temperature for 30 min in TBST containing a 1:5,000 dilution of alkaline phosphatase-coupled goat anti-rabbit antibody (Promega, Middletown, Wis.). The membrane was washed again and the immunoreactive bands visualized by soaking the membrane in 10 ml alkaline phosphatase substrate (Promega) containing nitroblue tetrazolium (NBT) and 5-bromo-4-chloro-3-indolylphosphate (BCIP). Color development was stopped by rinsing the membrane with water. A set of prestained SDS-PAGE standard proteins (SeeBlue, Novex) were used for molecular weight estimation.

Analysis of the primary sequence of Obg revealed a central portion of the protein which contained sequences identified as the GTP-binding domain (FIG. 1). Obg has been shown to hydrolyze GTP in *B. subtilis*. Welsh et al., "Biochemical Characterization of the Essential GTP-Binding Protein Obg of *Bacillus subtilis*", J. Bacteriol., Vol. 176, pp. 7161–68, 1994. Accordingly, we examined the ability of purified *S. aureus* Obg to hydrolyze GTP. Following incubation with γ32P-GTP under standard conditions, purified Obg was shown to catalyze release of labeled inorganic phoshate (Pi). The hydrolysis of GTP by *S. aureus* Obg was found to be linear with respect to protein concentration (data not shown). Further kinetic analysis of the GTPase activity of Obg is currently being investigated.

The far ultraviolet CD spectra of purified bacterially expressed *S. aureus* Obg protein was also investigated. A highly purified preparation of Obg protein was eluted from a $Ni^{++}$ affinity column. Far ultraviolet circular dichroism spectra were determined on an AVIV 62DS circular dichroism spectrometer (Aviv Associates, Inc., Lakewood, N.J.) at 4° C. using a 1 cm optical path length cuvette. Protein concentration was determined by the Bradford method, as understood in the art. Concentration of Obg was adjusted to 0.05 mg/ml in 10 mM NaPi, 0.5 M NaCl and 10% glycerol, pH 8.0. As shown in FIG. 5, the far ultraviolet CD spectra (200–260nm) of purified Obg showed distinctive double minima at 222 and 208 nm characteristic of alpha-helical secondary structure.

It should be understood that the present invention contemplates various polypeptides, such as the polypeptide having the deduced amino acid sequence as set forth in SEQ ID NO:2, as well as fragments, derivatives and analogs of such polypeptide, as previously defined. The polypeptides of the present invention may be recombinant polypeptides, natural polypeptides or synthetic polypeptides, such as those produced by conventional peptide synthesizers. The polypeptides, as well as polynucleotides, of the present invention are preferably purified to homogeneity and are provided in an isolated form, meaning that the material is removed from its original environment (e.g. the polypeptide is separated from coexisting materials in a natural system, or incorporated in a vector or composition that is not part of its natural environment). It should further be understood that the present invention contemplates polypeptides comprising Staphylococcal GTP-binding protein generally, as well as *S. aureus* GTP-binding protein in particular.

III. Methods for Using Staphylococcal Obg protein in High-throughput Screening Assays The present invention also contemplates the use of the polypeptides according to the present invention with screening procedures to identify antimicrobial agents effective against Staphylococcal bacterial strains, such as *S. aureus*. While the preferred embodiments of the invention utilize the *S. aureus* bacterial strain, it should be understood that the present invention is contemplated for use with other types of Staphylococcal bacterial strains.

In particular, the present invention contemplates the use of Staphylococcal GTP-binding protein as a novel therapeutic target in affinity-based pharmacological screening procedures for the discovery of antibiotics active against *S. aureus* and other Staphylococcal bacterial strains. Exemplary screening procedures known in the art are recited in U.S. Pat. Nos. 5,585,277 and 5,679,582 to Bowie et al., and are incorporated herein by reference.

The present invention provides methods for identifying pharmaceutically suitable antimicrobial compounds that act by inhibiting the function of the GTP-binding protein encoded by the Staphylococcal obg gene. One method for high-throughput screening involves identifying target compounds which bind to Obg protein thereby to inhibit GTP-binding function that is essential for cell growth and/or viability. Such compounds which bind with Obg are potential candidates for investigation as antimicrobial agents.

In particular, the present invention contemplates a method wherein a test compound is incubated with Staphylococcal GTP-binding protein to form a test combination. A control group of GTP-binding protein may be provided for comparison with the test combination. The method includes determining whether the test compound binds with Staphylococcal GTP-binding protein, which may be accomplished by various methods as known in the art for identifying ligands of target proteins. A test compound which binds with Staphylococcal GTP-binding protein is identified as a potential inhibitor of Obg protein function in a Staphylococcal bacterial strain, and therefore is a potential antimicrobial candidate.

One particular method for determining whether a test compound binds with Staphylococcal GTP-binding protein involves the step of increasing the temperature of a test combination wherein GTP-binding protein and test compound are present and increasing the temperature of a control group wherein GTP-binding protein is present, but the test compound is absent. A test compound which binds with GTP-binding protein is identified when protein unfolding due to denaturation from increasing temperature, e.g., biophysical catalization unfolding, occurs at a higher measured temperature in the test combination compared to the control group. Stated differently, a test compound which binds the Obg protein will increase the temperature at which the protein unfolding occurs, as a result of the binding test compound preventing or retarding the protein unfolding process at a given temperature. Accordingly, identifying those test compounds for which protein unfolding occurs at a higher temperature in the presence of test compound relative to the absence of test compound provides a method for screening test compounds to identify potential antimicrobial agents.

Preferably, the screening methods of the present invention are adapted to a high-throughput format, allowing a multiplicity of compounds to be analyzed in a single assay. Such inhibitory test compounds may be found in, for example, naturally occurring libraries, fermentation libraries encompassing plants and microorganisms, compound files, and synthetic compound libraries. Such compound libraries are commercially available from a number of known sources. The compounds identified using the methods of the present invention discussed above may be modified to enhance potency, efficacy, uptake, stability and suitability for use in pharmaceutical formulations and the like. These modifications are achieved and tested using methods well-known in the art.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. An isolated polynucleotide that encodes a Staphylococcal GTP-binding protein, wherein said polynucleotide:
   a) comprises a nucleic acid sequence as set forth in SEQ ID NO:1;
   b) encodes a polypeptide consisting essentially of an amino acid sequence as set forth in SEQ ID NO:2; or
   c) comprises a nucleic acid sequence which encodes the same protein as (a) or (b), but which is degenerate in accordance with the degeneracy of the genetic code.

2. The isolated polynucleotide of claim 1, wherein said polynucleotide comprises a Staphylococcal GTPase obg gene.

3. The isolated polynucleotide of claim 1, wherein said polynucleotide comprises a Staphylococcus aureus GTPase obg gene.

4. An isolated polymicleotide that is a DNA strand fully complementary to the polynucleotide of claim 1.

5. An isolated recombinant expression vector comprising an isolated polynucleotide that encodes a Staphylococcal GTP-binding protein, wherein said polynucleotide:
   a) comprises a nucleic acid sequence as set forth in SEQ ID NO: 1;
   b) encodes a polypeptide consisting essentially of an amino acid sequence as set forth in SEQ ID NO:2; or
   c) comprises a nucleic acid sequence which encodes the same protein as (a) or (b), but which is degenerate in accordance with the degeneracy of the genetic code.

6. The recombinant expression vector of claim 5, wherein said isolated polynucleotide comprises a Staphylococcal GTPase obg gene.

7. The recombinant expression vector of claim 5, wherein said isolated polynucleotide comprises a Staphylococcus aureus GTPase obg gene.

8. The recombinant expression vector of claim 5, wherein said expression vector is a plasmid.

9. The recombinant expression vector of claim 5, wherein said expression vector is a pET14b plasmid.

10. The recombinant expression vector of claim 5, wherein said isolated polynucleotide encodes a polypeptide that includes at least one histidine.

11. The recombinant expression vector of claim 5, wherein said isolated polynucleotide encodes a polypeptide that includes a thrombin cleavage site.

12. A recombinant expression vector, comprising an isolated polynucleotide that is a DNA strand fully complementary to the polynucleotide of claim 1.

13. An engineered host cell, wherein said cell comprises an isolated polynucleotide that encodes a Staphylococcal GTP-binding protein, wherein said polynucleotide:
   a) comprises a nucleic acid sequence as set forth in SEQ ID NO:1;
   b) encodes a polypeptide consisting essentially of an amino acid sequence as set forth in SEQ ID NO:2; or
   c) comprises a nucleic acid sequence which encodes the same protein as (a) or (b), but which is degenerate in accordance with the degeneracy of the genetic code.

14. The engineered host cell of claim 13, wherein said polynucleotide comprises a Staphylococcal GTPase obg gene.

15. The engineered host cell of claim 13, wherein said polynucleotide comprises a Staphylococcus aureus GTPase obg gene.

16. The engineered host cell of claim 13, wherein said host cell is a bacterial cell.

17. The engineered host cell of claim 13, wherein said cell is an E. coli bacterial cell.

18. The engineered host cell of claim 13, wherein said isolated polynucleotide is introduced into said host cell by a vector.

19. The engineered host cell of claim 18, wherein said vector includes a regulatory sequence operatively linked to said isolated polynucleotide.

20. The engineered host cell of claim 19, wherein expression in said host cell of said isolated polynucleotide is inducible by addition of an inducing agent appropriate to said regulatory sequence.

21. An engineered host cell, comprising an isolated polynucleotide that is a DNA strand fully complementary to the polynucleotide of claim 1.

22. A method of producing a Staphylococcal GTP-binding protein, comprising the steps of:
   a) introducing into suitable host cells an isolated polynucleotide that encodes a Staphylococcal GTP-binding protein; and
   b) culturing said host cells under conditions in which said host cells express said polynucleotide to produce said Staphylococcal GTP-binding protein; wherein said polynucleotide:
      a) comprises a nucleic acid sequence as set forth in SEQ ID NO:1; or
      b) encodes a polypeptide consisting essentially of an amino acid sequence as set forth in SEQ ID NQ:2.

23. The method of claim 22, wherein said polynucleotide comprises a Staphylococcal GTPase obg gene.

24. The method of claim 22, wherein said polynucleotide comprises a Staphylococcus aureus GTPase obg gene.

25. The method of claim 22, wherein the method includes the step of recovering said Staphylococcal GTP-binding protein.

26. The method of claim 22, wherein the step of introducing is accomplished with a suitable expression vector.

27. The method of claim 26, wherein said expression vector is a pET14b plasmid.

28. The method of claim 22, wherein said host cells are bacterial cells.

29. The method of claim 22, wherein said host cells are *E. coli* bacterial cells.

30. The method of claim 22, wherein said host cells are *E. coli* BL21(DE3)pLysS bacterial cells.

31. The method of claim 22, wherein the step of culturing includes contacting said host cells with an inducing agent, thereby to induce expression of said polynucleotide.

32. The method of claim 22, wherein said inducing agent is isopropylthiogalactoside (IPTG).

33. A method of producing a Staphylococcal GTP-binding protein, comprising the steps of:

a) introducing into suitable host cells an isolated polynucleotide of claim 1; and b) culturing said host cells under conditions in which said host cells express said polynucleotide to produce said Staphylococcal GTP-binding proteins.

34. A method of producing a Staphylococcal GTP-binding protein, comprising the steps of:

a) introducing into suitable host cells an isolated polynucleotide comprising a DNA strand fully complementary to the polynucleotide of claim 1; and b) culturing said host cells under conditions in which said host cells express said polynucleotide to produce said Staphylococcal GTP-binding protein.

* * * * *